United States Patent [19]

Lewis et al.

[11] Patent Number: 5,550,272

[45] Date of Patent: Aug. 27, 1996

[54] METHOD FOR HYDROSILATING UNSATURATED MONOMERS

[75] Inventors: Larry N. Lewis, Scotia; Terrell W. Carothers, Clifton Park, both of N.Y.

[73] Assignee: General Electric Company, Schenectady, N.Y.

[21] Appl. No.: 538,149

[22] Filed: Oct. 2, 1995

[51] Int. Cl.$^6$ .................................. C07F 7/08; C07F 7/10
[52] U.S. Cl. .................... 556/479; 556/415; 556/416; 556/419; 556/420; 556/421; 556/422; 556/425; 556/428; 528/15
[58] Field of Search ................................. 556/479, 425, 556/426, 419, 421, 420, 422, 428; 528/15

[56] References Cited

U.S. PATENT DOCUMENTS 2,823,218  2/1958  Speier et al. ............................ 556/479
4,785,066  11/1988  Maxson ................................... 528/15
5,206,402  4/1993  McVannel et al. ..................... 556/479

OTHER PUBLICATIONS

Chemical Abstract 124:56296 "Preparation of Double Bond-–Containing Organic Silicon Compounds", 1993.

Benkeser et al., Journal of the American Chemical Society, 80 (1959), pp. 5298–5300.

*Primary Examiner*—Paul F. Shaver
*Attorney, Agent, or Firm*—Edward A. Squillante, Jr.; William H. Pittman

[57] ABSTRACT

A method for silating unsaturated monomers by contacting a system having at least one SiH group, an unsaturated monomer, a transition metal catalyst and a free radical polymerization inhibitor is described.

15 Claims, No Drawings

1

METHOD FOR HYDROSILATING UNSATURATED MONOMERS

FIELD OF THE INVENTION

This invention relates to a novel method for silating unsaturated monomers. More particularly, the instant invention is directed to hydrosilating unsaturated monomers via a non-free radical mechanism in the presence of free radical polymerization inhibitors.

BACKGROUND OF THE INVENTION

Hydrosilations are defined as addition reactions involving organic and inorganic silicon hydrides and systems with multiple bonds. They can proceed via free radical mechanisms; however, as reported in the *Comprehensive Handbook on Hydrosilation* (Pergamon Press, 1992), such hydrosilations proceed via predominantly polar mechanisms when catalyzed by transition metal salts and complexes.

It is desirable to hydrosilate compounds in order to introduce, to the compounds, silicon-carbon bonds. The resulting compounds, for example, may be used as functionalized precursors to be incorporated into resin materials.

Often, however, it is known that hydrosilations of unsaturated monomers lead to competing undesired polymerizations and/or crosslinking of the monomers. These resulting polymerized and/or crosslinked monomers can gel, resulting in an undesired product.

The instant invention, therefore, is directed to a novel process for hydrosilating unsaturated monomers which unexpectedly results in a decrease in polymerization and/or crosslinking.

DESCRIPTION OF THE PRIOR ART

Efforts have been described for preventing polymerizations of monomers. In Chemical Abstracts 90:72633q, polymerization inhibitors are used in processes for making methacrylic acid from methacrolein.

Other efforts have been described for the addition of SiH compounds to unsaturated linkages. In the *Journal of the American Chemical Society*, 80 (1959), page 5298, the addition of silicochloroform to acetylenes is described.

SUMMARY OF THE INVENTION

The instant invention is directed to a process for hydrosilating unsaturated monomers under non-free radical conditions. Said process comprises the step of contacting:

(a) a system comprising at least one SiH group, (b) an unsaturated monomer, (c) a transition metal catalyst; and (d) a free radical polymerization inhibitor.

In the invention, it has been unexpectedly discovered that when free radical polymerization inhibitors are present during the transition metal catalyzed hydrosilation of unsaturated monomers, addition products are produced in the absence of polymer formation, notwithstanding that the reaction proceeds via a non-free radical mechanism.

DETAILED DESCRIPTION OF THE PREFERRED EMBODIMENT

System, as used herein, is not limited and preferably defined to mean compounds, resins and polymers. There is essentially no limitation with respect to the system comprising at least one SiH group employed in this invention other than that it is capable of hydrosilating the unsaturated monomers in the presence of a transition metal catalyst.

The system comprising at least one SiH group is preferably selected from the group consisting of (i) $(R)_{4-n}Si(H)_n$, (ii) $(R)_{3-n}(OR)_nSiH$, (iii) a resin comprising at least one SiH group; and (iv) a silicon polymer comprising at least one SiH group, wherein each R is independently a hydrogen, halogen, $C_{1-18}$ alkyl; substituted or unsubstituted aryl, or siloxy group. n is independently 0,1,2 or 3.

The compounds as depicted in (i) and (ii) are commercially available and prepared via conventional methods which generate carbon-silicon bonds. Such reactions include metalation reactions involving organometallic compounds and a proton transfer.

"Resins" as used herein are defined to mean three dimensional polymers (poly(organosiloxanes)) displaying branching. The resins comprising at least one SiH group can be described via the art recognized convention for designating silicone structural units in accordance with the number of oxygen atoms attached to the silicon. The convention uses the letters M, D, T and Q to designate said number of oxygen atoms as abbreviations for "mono", "di", "tri" and "quatro". Moreover, expressions such as "$M^{vi}$" and "$D^H$" denote an appropriate unit respectively having one vinyl group or one hydrogen atom attached to silicon. A more detailed description of the above convention for designating silicone structural units may be found in art recognized chemical encyclopedias such as *Kirk-Othmer Encyclopedia of Chemical Technology*, Vol, 20.

Such resins comprising at least one SiH group are not limited and preferably are comprised of chemically combined M and Q units, or M, Q, D and T units, where the M units and the D units can be the same or different, Q is $SiO_2$, M is $(R^1)_a(R^3)_b$-$SiO_{0.5}$, D is $(R^1)_c(R^2)_d SiO$, and T is $R*SiO_{1.5}$, each $R^1$ and $R^2$ is independently a hydrogen, $C_{1-18}$ alkyl or substituted or unsubstituted aryl with the proviso that there is at least one SiH group on the resin, "a" is a whole number equal to 0 to 3 inclusive, "b" is a whole number equal to 0 to 3 inclusive, and the sum of a+b is equal to 3, c is a whole number equal to 0 to 2 inclusive, d is a whole number equal to 0 to 2 inclusive and the sum of c+d is equal to 2. In preferred instances, from 0 to up to about 25 mole percent of $R*SiO_{1.5}$ units are present in the resin based on the total moles of siloxy units, where $R*$ is selected from $R^1$ and $R^2$.

Radicals included with $R^1$, $R^2$ and $R*$ are, for example, $C_{(1-8)}$ aliphatic radicals, such as alkyl radicals, like, methyl, ethyl, propyl and butyl; haloalkyl, such as trifluoropropyl; aromatic radicals, such as phenyl, tolyl, xylyl and naphthyl radicals; again, with the proviso that at least one SiH group is present on the resin.

The preferred MQ resin is in the form of a toluene dispersible silicon hydride containing organosiloxane hydrolyzate. The organosiloxane hydrolyzate can contain from about 0.2% to about 5%, and preferably from about 1% to about 3% by weight of hydroxy group based on the total weight or organosiloxane resin.

The resins described in this invention may be prepared, for instance, by reacting, under acidic conditions, a silica hydrosol with a source having triorganosiloxy units. A more detailed description may be found in U.S. Pat. No. 2,676,182, the disclosure of which is incorporated herein by reference.

The silicon polymers which may be employed in this invention are not limited and they may be high viscosity gum-like polymers and fluid polymers. They may be differentiated from resins in that the former are defined herein to mean polymers which are two dimensional and essentially do not display branching. Often, however, they are poly(organosiloxane) fluids which have a viscosity of from about 1 to about 1,500 centipoise and preferably from about 10 to about 1,000 centipoise at 25° C. Typical poly(organosiloxane) fluids which may be employed in this invention often have the formula:

$$R^4-\underset{\underset{R^4}{|}}{\overset{\overset{R^4}{|}}{Si}}O\left[\underset{\underset{R^4}{|}}{\overset{\overset{R^4}{|}}{Si}}O\right]_t\underset{\underset{R^4}{|}}{\overset{\overset{R^4}{|}}{Si}}-R^4 \qquad I$$

where each $R^4$ is independently selected from hydrogen, $C_{(1-13)}$ monovalent organic radicals free of olefinic unsaturation with the proviso that at least one $R^4$ is hydrogen, and t is a positive integer having a value sufficient to provide a poly(organosiloxane) viscosity of from about 1 to 1,500 centipoise at 25° C. Preferably, each $R^4$ is independently selected from hydrogen, alkyl radicals of 1 to 8 carbon atoms, such as methyl, ethyl, propyl; cycloalkyl radicals, cycloheptyl, unsubstituted or substituted aromatic radicals and haloalkyl radicals such as 3,3,3-trifluoropropyl, again, with the proviso that at least one $R^4$ is hydrogen.

A more detailed description of the resins and polymers employed in this invention as well as their preparation may be found in U.S. Pat. No. 5,410,007, the disclosure of which is incorporated herein by reference.

The unsaturated monomers which may be employed in this invention are not limited. In fact, any unsaturated monomer capable of being hydrosilated may be employed. The often preferred group of unsaturated monomers include those represented by the formulae

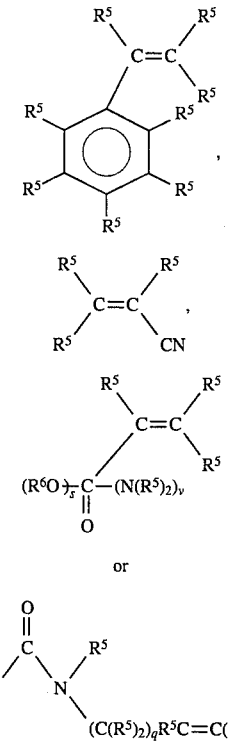

wherein each $R^5$ is independently a hydrogen, lower alkyl ($C_{1-5}$ hydrocarbon), halogen, nitrile group (—CN), nitro group (—NO$_2$), amide group

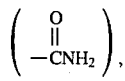

amine group (—NH$_2$), sulfonate group (—SO$_3R^6$), ester group

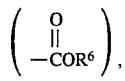

allyl group $((R^5)_2C=CR^5(C(R^5)_2)_{\overline{q}}$ where q is 0 to 5, s and v are 0 or 1 but not simultaneously 0 or simultaneously 1 and each $R^6$ is independently a hydrogen or lower alkyl as defined above.

Further, it is often preferred that the compounds represented by the formulae above are styrene, acrylonitrile, methacrylonitrile, methyl methacrylate, allylmethacrylate, methacrylamide or acrylamide or N-vinyl formamide.

There is no limitation with respect to the transition metal catalysts employed in this invention other than that they are capable of catalyzing hydrosilations via non-free radical mechanisms.

An illustrative list of the transition metal catalysts which may be employed in this invention include, for instance, group VIII compounds such as RhCl$_3$, Rh(PPh$_3$)$_3$Cl (where Ph is a phenyl group), H$_2$PtCl$_6$, soluble platinum catalysts including Speier's catalyst (H$_2$PtCl$_6$ in i-PrOH), Karstedt's catalyst (the reaction product of H$_2$PtCl$_6$ and divinyltetramethyldisiloxane as described in U.S. Pat. Nos. 3,715,334 and 3,775,452 the disclosures of which are incorporated herein by reference), Ashby's catalyst (the reaction product of H$_2$PtCl$_6$ and tetravinyltetramethyldisiloxane as described in U.S. Pat. Nos. 3,159,601 and 3,159,662 the disclosures of which are incorporated herein by reference) and Lamoreoux's catalyst (H$_2$PtCl$_6$ in n-octanol as described in U.S. Pat. No. 3,220,972 the disclosure of which is incorporated herein by reference).

Additional catalysts which may be employed in this invention include those described in U.S. Pat. No. 5,410,007 the disclosure of which is incorporated herein by reference.

There is no limitation to the free radical polymerization inhibitors (often referred to as spin traps) employed in this invention, other than that they do not interfere with the hydrosilations of the unsaturated monomers.

Illustrative examples of the free radical polymerization inhibitors which may be used in the practice of this invention include galvinoxyl, 2,2,6,6-tetramethylpiperidinyloxy (TEMPO) having the formula

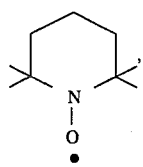

4-hydroxy(2,2,6,6-tetramethylpiperidinyloxy (4-OH TEMPO) having the formula

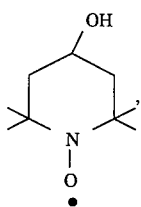

bis(4-hydroxy-tetramethylpiperidinyloxy) diradical, 2,2-diphenyl-1-picrylhydrazyl(DPPH), having the formula

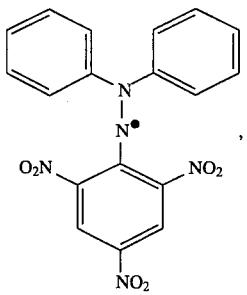

Banfield's Radical having the formula

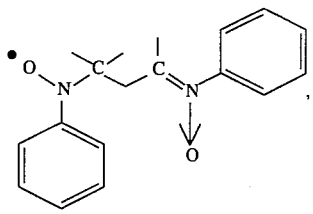

1,3,5-triphenyl verdazyl having the formula

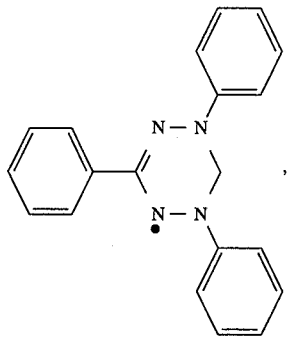

Koelsch's radical having the formula

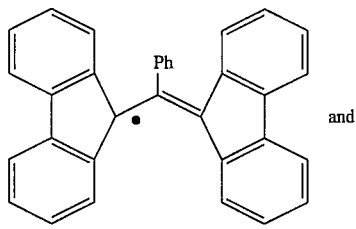

and 1-nitroso-2-naphthol having the formula

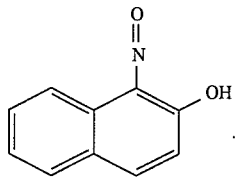

In addition, benzofuroxan, other nitroso compounds such as, nitrosobenzene and 2-methyl-2-nitroso propane dimer (Ntb), and nitrones, such as N-t-butyl-α-phenylnitrone can be used. Further, it is within the scope of the invention to employ any of the substituted reaction products of the above free radical polymerization inhibitors with the proviso that they do not interfere with the hydrosilations of this invention.

When silating the unsaturated monomers in this invention, any reaction vessel conventional in the art may be employed. The reaction vessel may be charged with the system comprising at least one SiH group, the unsaturated monomer, the transition metal catalyst and the free radical polymerization inhibitor, the particular order of addition not being limited. Stirring may be employed but is not required in order to enhance the reaction. Moreover, the hydrosilation reaction may be conducted at ambient temperature to about 200° C. However, temperatures between about 20° C. and 125° C. are often preferred. Additionally, the reaction may occur at atmospheric pressure; however, the pressure may be increased if desired, and substantially inert organic solvents like toluene may also be used to enhance the reaction conditions.

The amount of system comprising at least one SiH group, unsaturated monomer, transition metal catalyst and free radical polymerization inhibitor employed in the invention is not limited. The only requirement is that the desired hydrosilation reactions can occur.

The following examples are provided to further illustrate and facilitate the understanding of the instant invention. All products obtained may be confirmed via conventional techniques which include proton and carbon 13 nuclear magnetic resonance spectroscopy.

EXAMPLE 1

A reaction bomb was charged with 75.6 grams ($4.1 \times 10^{-2}$ moles) of a SiH stopped silicon fluid ($^H MD_{23}M^H$), 10 mL of acrylonitrile and 1.4 mL of Karstedt's catalyst (a 5.49% by weight Pt solution in xylene, 0.42 mmol Pt), producing a reaction mixture. The reaction mixture was heated to 111° C. for 18 hours and the resulting product was a gelled silicone which displayed inclusions of solid poly( acrylonitrile ).

EXAMPLE 2

A reaction bomb was charged with 53.4 grams ($2.9 \times 10^{-2}$ moles) of a SiH stopped silicon fluid ($^H MD_{23}M^H$), 10 mL of acrylonitrile, 0.09 grams ($0.49 \times 10^{-3}$) moles) of 4-OH TEMPO and 1.5 mL of Karstedt's catalyst (5.49% by weight Pt solution in xylene, 0.42 mmol Pt), producing a reaction mixture. The reaction mixture was heated to 111° C. for 2 hours and the product obtained was a viscous silicone oil (56.9 grams, 0.029 moles) and 100% conversion of SiH moieties to —CH(CH$_3$)CN groups were observed. $^1$H and $^{13}$C NMR analysis indicated all hydrosilations were found to be regioselective yielding alpha addition products.

EXAMPLE 3

A reaction bomb was charged with 98.7 g of a SiH containing resin (MM$^H$DQ, general formula M$_{0.50}$M$^H_{0.32}$D$_{0.08}$Q, M$_w$=2,800), 100 mL of acrylonitrile, 75 mL toluene and 0.5 mL Karstedt's catalyst (5.49% by weight Pt solution in xylene, 0.14 mmol Pt), producing a reaction mixture. The reaction mixture was heated to 112° C. for 3 days and a gelled product, insoluble in organic solvents, was obtained.

EXAMPLE 4

Example 4 was conducted in a manner similar to the one described in Example 3 except that 101.43 g of resin was used, 50 mL of toluene were used and 0.12 g (0.69×10$^{-3}$ moles) of 4-OH TEMPO were employed. The resulting product was 65.4 grams of cyano-functionalized MDQ resin (general formula M$_{0.5}$M$^H_{0.27}$M$^{CN}_{0.05}$D$_{0.08}$Q, M$_w$=10,700). All hydrosilation reactions were found to be regioselective with $^1$H and $^{13}$C NMR analysis giving exclusively alpha addition products with approximately 16% conversion of SiH moieties to —CH(CH$_3$)CN groups.

EXAMPLE 5

A reaction flask having a dry ice condenser, magnet stir bar and a pressure equalizing dropping funnel, was charged with 23.45 g (0.186 mol) allylmethacrylate, excess (CH$_3$)$_2$SiHCl in the presence of Karstedt's catalyst (100 mL of a 6.5% by weight Pt solution in xylene, 31 mmol Pt) and 100 mL of toluene, producing a mixture. The mixture was heated to 112° C. resulting in an exotherm and gellation.

EXAMPLE 6

Example 6 was conducted in a manner similar to the one described in Example 5 except that 0.5 g of 4-OH TEMPO were employed. The resulting product was 27.4 g methacryloxypropyldimethylsilylchloride.

EXAMPLE 7

A reaction flask equipped with a dry ice condenser, magnetic stir bar and a thermometer, was charged with 72.4 g (6.22×10$^{-1}$ moles) of triethylsilane and 50.0 g (5.87×10$^{-1}$ moles) of methacrylamide in the presence of Karstedt's catalyst (1.5 mL of a 5.49% by weight Pt solution in xylene, 0.42 mmol Pt). The mixture was reacted in refluxing tetrahydrofuran for 6 hours. The resulting product was a mixture of unreacted silicone fluid, (beta addition) and poly(methacrylamide).

EXAMPLE 8

Example 8 was conducted in a manner similar to the one described in Example 7 except that 0.14 grams (0.80×10$^{-3}$ moles) of 4-OH TEMPO were employed. The resulting product was a silicone fluid (76.53 grams, 0.38 moles) which showed ~95% conversion of Si-H moieties to —CH$_2$CH(CH$_3$)CONH$_2$ groups with 5% Si-H conversion to —C(CH$_3$)$_2$CONH$_2$ groups (addition structures confirmed by $^1$H and $^{13}$C NMR analyses).

EXAMPLE 9

A reaction flask equipped with a dry ice condenser, magnetic stir bar and a thermometer, was charged with 75.6 g (9.23×10$^{-1}$ moles) of triethylsilane and 107.43 g (1.07 moles) of methylmethacrylate in the presence of Karstedt's catalyst (1.5 mL of a 5.49% by weight Pt solution in xylene, 0.42 mmol Pt). The mixture was reacted at ambient temperature for 14 hours. The resulting product was a mixture of unreacted silicone fluid, undetermined oligomers and solid poly(methylmethacrylate).

EXAMPLE 10

Example 10 was conducted in a manner similar to the one described in Example 9 except that 0.09 grams (0.54×10$^{-3}$ moles) of 4-OH TEMPO were employed. The resulting product was a silicone fluid (165.6 grams, 0.766 moles) which showed ~100% conversion of Si-H moieties to —CH$_2$CH(CH$_3$)COOCH$_3$ groups (exclusive beta addition confirmed by $^1$H and $^{13}$C NMR analyses).

What is claimed is:

1. A process for hydrosilating unsaturated monomers under non-free radical conditions comprising the step of contacting:

(a) a system comprising at least one SiH group, (b) an unsaturated monomer, (c) a transition metal catalyst; and (d) a free radical polymerization inhibitor.

2. A process for hydrosilating unsaturated monomers in accordance with claim 1 wherein said system comprising at least one SiH group is selected from the group consisting of (i) (R)$_{4-n}$Si(H)$_n$, (ii) (R)$_{3-n}$(OR)$_n$SiH, (iii) a resin comprising at least one SiH group; and (iv) a silicon polymer comprising at least one SiH group,
      wherein each R is independently a hydrogen, halogen, C$_{1-18}$ alkyl substituted or unsubstituted aryl, nitrile or siloxy group and n is an integer from 0 to 3.

3. A process for hydrosilating unsaturated monomers in accordance with claim 2 wherein said system is a resin comprising at least one SiH group which is a three dimensional poly(organosiloxane) polymer displaying branching.

4. A process for hydrosilating unsaturated monomers in accordance with claim 3 wherein said poly(organosiloxane) polymers displaying branching are represented by the formula MQ or MM$^H$DQ.

5. A process for hydrosilating unsaturated monomers in accordance with claim 1 wherein said system is a silicon polymer comprising at least one SiH group which is a two dimensional poly(organosiloxane) polymer which does not display branching.

6. A process for hydrosilating unsaturated monomers in accordance with claim 5 wherein said poly(organosiloxane) polymer is a fluid having the formula

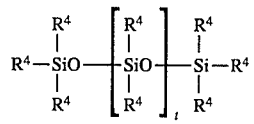

wherein each R$^4$ is independently selected from hydrogen, C$_{1-13}$ monovalent organic radicals free of olefinic saturation with the proviso that at least one R$^4$ is hydrogen, and t is a positive integer having a value sufficient to provide a fluid with a viscosity from about 1 to 1,500 centipoise at 25° C.

7. A process for hydrosilating unsaturated monomers in accordance with claim 1 wherein said unsaturated monomer is represented by the formulae

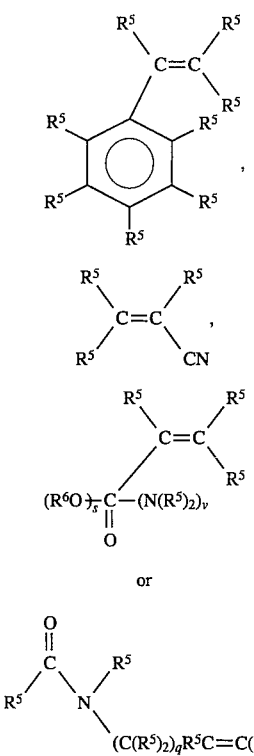

wherein each $R^5$ is independently a hydrogen, $C_{1-5}$ hydrocarbon, halogen nitrile group (—CN), nitro group (—NO$_2$), amide group (—NH$_2$), sulfonate group (—SO$_3R^6$), ester group,

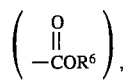

allyl group $((R^5)_2C=CR^5(C(R^5)_2)_q$—, $q$ is 0 to 5 and s and v are 0 or 1 but not simultaneously 0 or simultaneously 1 and each $R^6$ is independently a hydrogen, or $C_{1-5}$ hydrocarbon.

8. A process for hydrosilating unsaturated monomers in accordance with claim 7 wherein said unsaturated monomer is styrene, acrylonitrile, methacrylonitrile, methylmethacrylate, allylmethacrylate, methacrylamide, acrylamide or N-vinyl formamide.

9. A process for silating unsaturated monomers in accordance with claim 1 wherein said transition metal catalyst is $H_2PtCl_6$, $RhCl_3$, $Rh(PPh_3)_3Cl$, Speier's catalyst, Karstedt's catalyst, Ashby's catalyst or Lamoreoux's catalyst.

10. A process for hydrosilating unsaturated monomers in accordance with claim 1 wherein said free radical polymerization inhibitor is galvinoxyl, TEMPO, 4-OH TEMPO, DPPH, Banfield's radical, 1,3,5-triphenyl verdazyl, Koelsch's radical, 1-nitroso-2naphthol or any substituted reaction product thereof.

11. A process for hydrosilating unsaturated monomers in accordance with claim 10 wherein said free radical polymerization inhibitor is benzofuroxan, nitrosobenzene, Ntb or N-t-butyl-α-phenylnitrone.

12. A process for hydrosilating unsaturated monomers in accordance with claim 1 wherein said method is conducted in a reaction bomb.

13. A process for hydrosilating unsaturated monomers in accordance with claim 1 wherein said reaction is conducted at a temperature from about ambient temperature to about 200° C.

14. A process for hydrosilating unsaturated monomers in accordance with claim 1 wherein said reaction further comprises the step of stirring.

15. A process for hydrosilating unsaturated monomers in accordance with claim 1 wherein said reaction is conducted at atmospheric pressure.

* * * * *